United States Patent
Holmqvist (10) Patent No.: US 10,314,987 B2
(45) Date of Patent: Jun. 11, 2019

(54) MEDICAMENT DELIVERY DEVICE

(71) Applicant: Carebay Europe Ltd, Swatar (MT)

(72) Inventor: Anders Holmqvist, Värmdö (SE)

(73) Assignee: SHL Medical AG, Zug (CH)

(*) Notice: Subject to any disclaimer, the term of this patent is extended or adjusted under 35 U.S.C. 154(b) by 664 days.

(21) Appl. No.: 14/432,386

(22) PCT Filed: Sep. 30, 2013

(86) PCT No.: PCT/EP2013/070373
§ 371 (c)(1),
(2) Date: Mar. 30, 2015

(87) PCT Pub. No.: WO2014/053451
PCT Pub. Date: Apr. 10, 2014

(65) Prior Publication Data
US 2015/0273162 A1   Oct. 1, 2015

Related U.S. Application Data

(60) Provisional application No. 61/710,029, filed on Oct. 5, 2012.

(30) Foreign Application Priority Data

Oct. 5, 2012 (SE) ...................... 1251133

(51) Int. Cl.
*A61M 5/50* (2006.01)
*A61M 5/20* (2006.01)
(Continued)

(52) U.S. Cl.
CPC ........ *A61M 5/5086* (2013.01); *A61M 5/2033* (2013.01); *A61M 5/3157* (2013.01);
(Continued)

(58) Field of Classification Search
CPC ...... A61M 5/20; A61M 5/326; A61M 5/3272; A61M 5/2033; A61M 5/3157;
(Continued)

(56) References Cited

U.S. PATENT DOCUMENTS 5,820,602 A   10/1998   Kovelman et al.
2003/0105430 A1*  6/2003   Lavi ................... A61M 5/2033
                                                              604/136

(Continued)

FOREIGN PATENT DOCUMENTS

EP       2468336 A1    6/2012
WO    2009/062508 A1    5/2009

OTHER PUBLICATIONS

EPO, Int'l Search Report in PCT/EP2013/070373, dated Feb. 18, 2014.
EPO, Written Opinion in PCT/EP2013/070373, dated Feb. 18, 2014.

*Primary Examiner* — Kami A Bosworth
*Assistant Examiner* — Alexandra Lalonde
(74) *Attorney, Agent, or Firm* — McDonnell Boehnen Hulbert & Berghoff LLP (57) ABSTRACT

A medicament delivery device includes a housing adapted to receive a medicament container; an actuation member movable from a first position to a second position, such that the medicament is allowed to be expelled through the delivery member; and an interlock member movable between a locking position and a releasing position. The device has an indicator to show that it has been used provided by the actuation member's being retained in its second position. The actuation member includes at least one latching projection, and the drive mechanism includes corresponding latching surfaces, against which the latching projections latch when the actuation member is in its second position.

13 Claims, 9 Drawing Sheets

(51) Int. Cl.
*A61M 5/32* (2006.01)
*A61M 5/315* (2006.01)

(52) U.S. Cl.
CPC ....... *A61M 5/326* (2013.01); *A61M 2005/208* (2013.01); *A61M 2005/3267* (2013.01); *A61M 2205/583* (2013.01)

(58) Field of Classification Search
CPC ........ A61M 5/5086; A61M 2005/2013; A61M 2005/208; A61M 2005/2073
See application file for complete search history.

(56) References Cited

U.S. PATENT DOCUMENTS

| | | | |
|---|---|---|---|
| 2005/0101919 A1* | 5/2005 | Brunnberg | A61M 5/2033 604/197 |
| 2010/0185178 A1* | 7/2010 | Sharp | A61M 5/002 604/506 |
| 2011/0092915 A1* | 4/2011 | Olson | A61M 5/2033 604/198 |
| 2011/0144594 A1* | 6/2011 | Sund | A61M 5/2033 604/228 |
| 2012/0209192 A1* | 8/2012 | Alexandersson | A61M 5/2033 604/135 |

* cited by examiner

Fig. 9 under 35 U.S.C. 371 of the
MEDICAMENT DELIVERY DEVICE

CROSS-REFERENCE TO RELATED APPLICATIONS

This is the National stage filing under 35 U.S.C. 371 of the International Application PCT/EP2013/070373 filed Sep. 30, 2013 which claims benefit to U.S. provisional application 61/710,029 filed Oct. 5, 2012 and benefit under 35 U.S.C 119 (a-d) to SE1251133-3 filed Oct. 5, 2012.

TECHNICAL AREA

The present invention relates to a medicament delivery device and in particular a device provided with safety features for providing an intended user info of the status of the device.

BACKGROUND OF INVENTION

Medicament delivery devices for automatic or semi-automatic injection of medicaments have been known for many years. While the first generations of injectors merely designed to deliver a medicament as quickly as possible, increased use of the devices by patients in non-clinical settings has led to the necessity of providing further handling and safety functions.

Important handling and safety functions of medicament delivery devices include inhibiting premature actuation of the device (misfiring). To ensure that the medicament is properly injected, actuation of the device is inhibited until the auto-injector is correctly positioned at a dose delivery site. Furthermore, since the member delivering the medicament can be sharp and may be contaminated after the device has been actuated, devices that retract or cover the medicament delivery member when the device is withdrawn from the dose delivery site have been developed. To prevent that a person unintentionally contacts the medicament delivery member and to allow safely discarding the device, some devices feature a mechanism that locks the device once the medicament delivery member is covered or retracted.

Another important feature with medicament delivery devices is to prevent the risk of using, or trying to use, devices that already have been used, i.e. ensuring that an intended user is provided with information regarding the status of the device, and also providing inhibiting features after use of a medicament delivery device. Many medicament delivery devices are arranged with some sort of actuation mechanism, often including a push button or the like. Such push buttons are often positioned at a distal end of the device, furthest away from a dose delivery site such that a finger, often a thumb, may operate the button when holding the device. Such an arrangement is disclosed in the document EP 850079, in which a so called pen injector is disclosed having a dose setting mechanism comprising a dose setting knob at a distal end of the device. When turning the dose setting knob a dose of medicament is set. In order to deliver the dose, the dose setting knob is pressed in the proximal direction into an end position where it is axially locked. When a subsequent dose is to be delivered, the dose setting knob is again rotated, whereby it is unlocked and moved in the distal direction.

The device according to EP 850079 is intended for multiple doses, and therefore the dose setting knob has to be returned to its initial position. Even though locked after dose delivery, it is easy to unlock the button for the subsequent dose. For a medicament delivery device that is intended for a single dose, it should not be possible to manipulate the device such that the dose button may be returned. A user might then get the impression that the device has not been used and may try to administer a dose with a used device. If the user does not have access to another medicament delivery device, he may unexpectedly find himself lacking delivery devices to fulfil a medication scheme.

As shown above, available medicament delivery devices either do not provide the necessary handling, safety and information functions or they require cooperation of one or several complex mechanisms. Accordingly, there is a need for medicament delivery devices that comprise mechanisms providing some or all of these functions in a reliable manner, with as few parts as possible. This is especially important for single-use devices, where low manufacturing cost is a necessity.

BRIEF DESCRIPTION OF INVENTION

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site.

Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The aim of the present invention is to remedy the above mentioned drawbacks with the state of the art medicament delivery devices. This aim is obtained with a medicament delivery device according to the features of the independent patent claims. Preferable embodiments of the invention form the subject of the dependent patent claims.

According to a preferable solution, the present invention relates to a medicament delivery device, comprising a housing adapted to receive a medicament container. The medicament container may have a number of designs and may be of a number of sizes depending on intended use and type of medicament. A suitable medicament delivery member may be arranged to the medicament container. The delivery member may either be an integral part of the medicament container or it may be a connectable delivery member.

Further the medicament delivery member may be of a number of designs depending on the desired function and type of medicament, such as nozzles, mouth pieces, nebulizers, or injection needles, to mention a few.

The medicament delivery device according to the invention may preferably comprise a drive mechanism that is acted upon and in turn acts upon the medicament container. In this respect there may be a number of different designs that are within the reach of a person skilled in the art that may be utilized for performing a driving function for acting on the medicament container, whereby a dose of medicament delivered. These include different types of means with accumulated power, such as mechanical or gas spring means, just to mention a few.

Preferably, the medicament delivery device may further comprise an actuation member. It may be movable from a first position, in which it allows the drive mechanism to be retained, to a second position, in which it allows the drive mechanism to be released. When the drive mechanism is released, the medicament is allowed to be expelled through the delivery member. The actuation member may be of a number of designs. One preferred design is a push button that may be arranged at the distal end of the medicament delivery device and arranged to be depressed into the housing of the device when a dose is to be delivered.

According to a feasible solution of the invention, it may further comprise an interlock member movable between a locking position, at which it prevents movement of the actuation member from its first position to its second position, and a releasing position, at which it allows movement of the actuation member from its first position to its second position. This solution ensures that the actuation member may not be moved until the interlock member has been activated. The activation of the interlock member may be performed by different actions. A preferred action may be that the interlocking member is arranged with grooves in which protrusions of the actuation member are positioned, where the interlock member may be turned such that the protrusions of the actuation member are positioned such that the actuation member may be moved to the second position. Other feasible actions may be the pressing of the medicament delivery device against a dose delivery site, which action moves the interlock member out of blocking engagement with the actuation member.

Further, the device may have an indicator to show that it has been used and this is preferably provided by the actuation member being retained in its second position.

According to a preferable solution of the invention, it may be characterised in that the actuation member comprises at least one latching projection and the drive mechanism comprises corresponding latching surfaces against which the latching projections latch when the actuation member is in its second position. With this solution it may be ensured that the actuation member is safely retained in the second position, with the advantages that there is a clear and positive indication that the device has been used because the user immediately sees that the actuation member is depressed. Also, the lock mechanism ensures that it is very difficult to manipulate the actuation member. Instead, it is securely locked in the second position inside the housing of the medicament delivery device.

According to one preferable solution of the invention, the at least one latching projection comprises at least one flexible section and an end surface facing in the distal direction of the device.

Further, the at least one latching projection is integrated in proximally directed arms of the actuation member.

Moreover, said latching surfaces are facing in the proximal direction of the device, such that said surfaces are brought in latching engagement when said actuation member is in its second position.

According to one aspect of the invention, the drive mechanism comprises a holding member, a plunger member, a drive spring, and a signal generating member.

According to another aspect of the invention, the annular ledge is arranged with cut-outs having side surfaces and through which the proximally directed arms of the actuation member may extend.

According to a further aspect of the invention, the at least one latching projection is configured to be biased by the side surfaces when the actuation member is moved a certain distance from the first position to the second position and such that when the end surface of the at least one latching projection have passed the cut-outs, the flexible section will bias back the at least one latching projections whereby the end surface of the at least one latching projection latches with the proximally directed surfaces of the annular ledge.

According to another aspect of the invention, the actuation member comprises a generally tubular distal part forming a push button provided through the interlock member, said generally tubular distal part comprises protrusions on its outer surface configured to fit into transversally and longitudinally extending grooves of the interlock member.

According to yet another aspect of the invention, the interlock member is in the locking position, when the protrusions are positioned within the transversally extending grooves and the interlock member is in the releasing position, when the protrusions are positioned in line with the longitudinally extending grooves.

According to a further aspect of the invention, the holding member comprises at least one distally directed arm which may be flexible in the radial direction and wherein said at least one distally directed arm may be arranged with inwardly directed hooks designed to fit into cut-outs or through holes of the plunger rod and outwardly directed protrusions designed to interact with the inner surface of the actuation member and with through holes of the actuation member.

According to another aspect of the invention, the actuation member is in the first position when said actuation member is arranged surrounding said distally directed arms such that the hooks are engaged into the cut-outs or through holes of the plunger rod.

According to yet another aspect of the invention, the actuation member is in the second position when said push button is completely positioned within the interlock member such that the protrusions are allowed to come into the through holes whereby the arms are allowed to be moved radially outwards for allowing the hooks to come out of engagement with the plunger rod.

According to a further aspect of the invention, the medicament delivery device is an injection device and more particularly a pen injector or an auto-injector.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
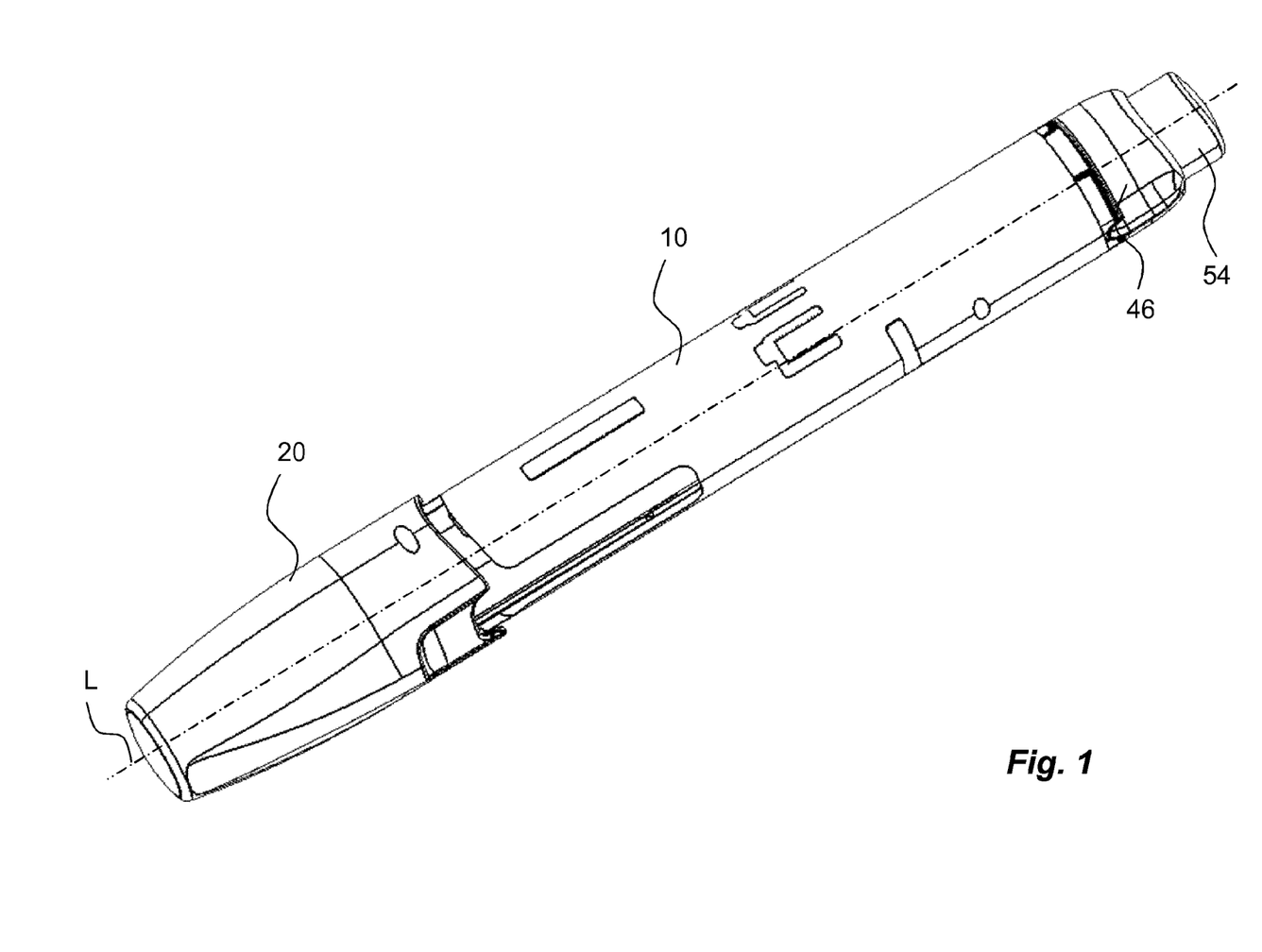
FIG. 1 is a perspective view of a medicament delivery device according to the present invention.

FIG. 1 shows a perspective view of a medicament delivery device according to the present invention. The device comprises a generally cylindrical elongated housing 10 having a proximal and distal end as seen along a longitudinal axis L of the device. The proximal end of the device may further be arranged with a protective cap 20.

Figure 2:
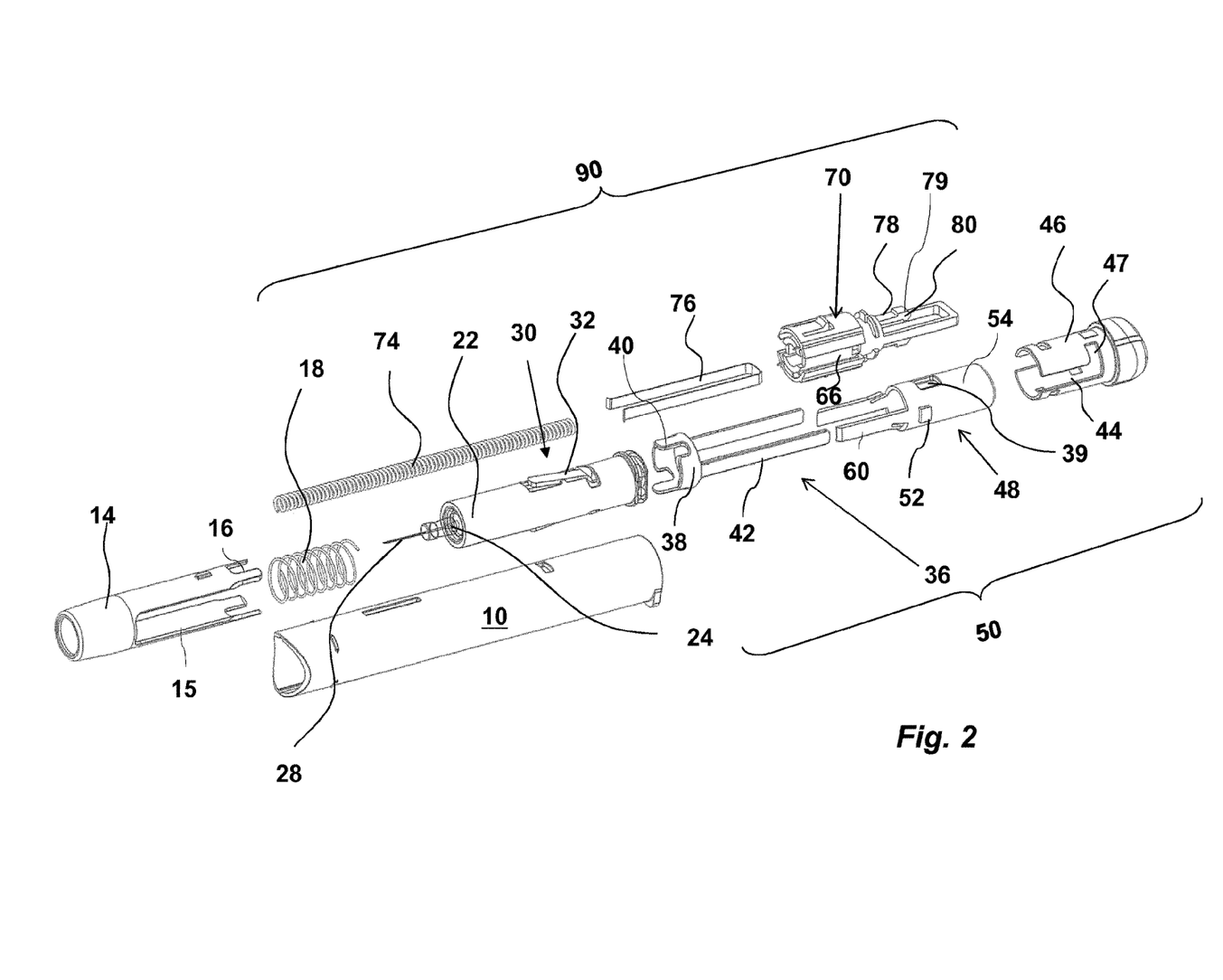
FIG. 2 is an exploded view of the device according to FIG. 1.

FIG. 2 shows an exploded view of the device according to FIG. 1. A guard 14 or sleeve-like structure, FIG. 2, is arranged slidable in the longitudinal direction inside the housing and through a proximal end passage. The guard 14 may be arranged with distally directed arms 15, wherein each arm is arranged with tongues 16 at their distal ends. The housing is adapted to receive a medicament container 24 with or without a connectable delivery member 28. A medicament container holder 22 is arranged within the housing and configured to receive the medicament container 24. The medicament container holder may be partially arranged in the guard 14 such that the guard is slidable in relation to both the medicament container holder and the housing. The medicament container 24 may comprise a movable stopper 26, FIG. 4, and a medicament delivery member 28. However, as stated above, the medicament delivery member 28 does not have to be part of the medicament container and may be an independent element of the device. As shown in FIG. 2, the medicament delivery member may be a needle. A guard spring 18 may be arranged between the proximal end of the medicament container holder 22 and an annular ledge on the inner surface at the proximal end of the guard for urging the guard 14 in the proximal direction. It is also possible that the guard spring 18 may be arranged between an annular ledge on the inner surface of the housing and an annular ledge on the inner surface at the proximal end of the guard.

Figure 3:
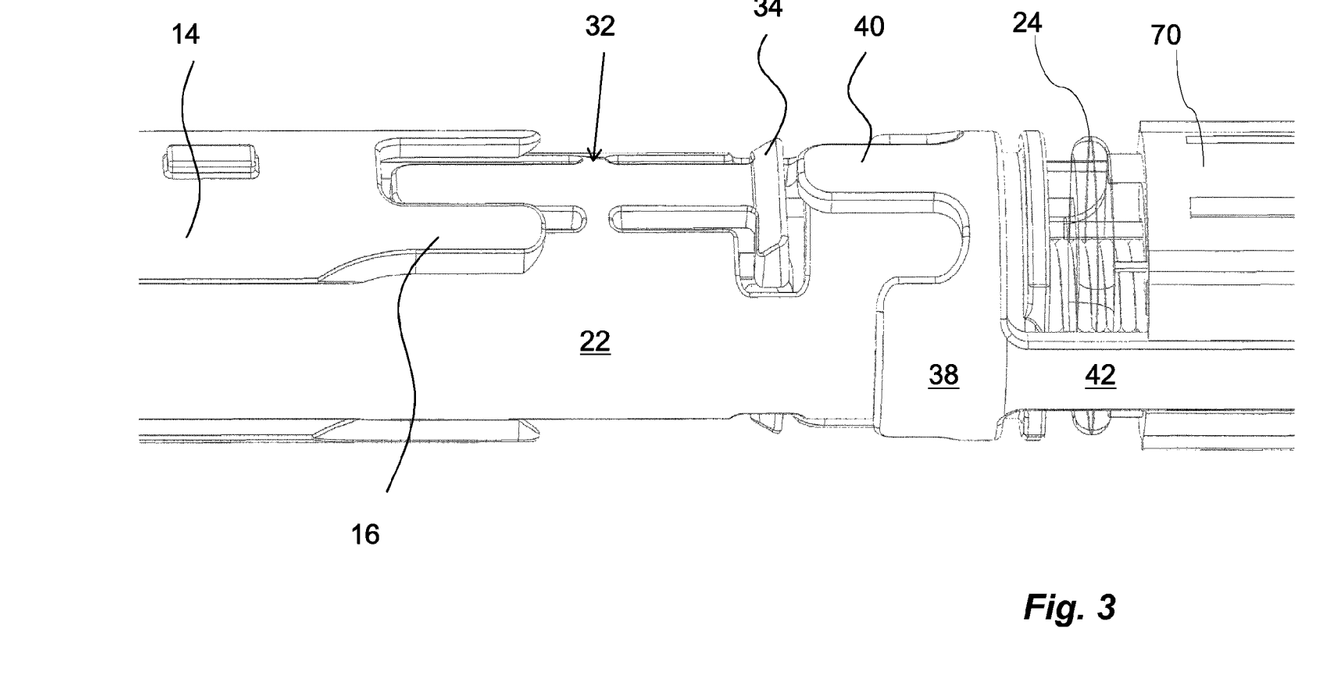
FIG. 3 is detailed view of a part of the device of FIG. 1.

A side surface of the medicament container holder 22 may be arranged with a locking mechanism 30, FIGS. 2 and 3. The locking mechanism 30 comprises at least one lever. The lever may be a see-saw. The lever may have the form of a longitudinally extending beam 32. The beam 32 may be connected at the middle thereof to the medicament container holder 22 by two pivot arms, creating a proximal end and a distal end. The beam may be formed integral with the medicament container holder 22 or pivotally engaged therewith. The distal end of the beam 32 may be arranged with a transversally extending ledge 34, FIG. 3. The guard 14 may be arranged such in relation to the beam 32 that the tongues 16 are aligned along the sides of the beam 32, as will be explained further below.

Furthermore, the device may be provided with an actuation mechanism 50 comprising an actuation locking member 36, an interlock member 46 in the form of a guide sleeve, and an actuation member 48. The actuation locking member 36 may comprise a generally ring-shaped or sleeve-shaped member 38 surrounding the medicament container holder 22 and positioned distally in relation to the beam 32, FIG. 3. The ring-shaped member 38 may have at least one proximally extending tongue 40 arranged in line with the beam 32. The ring-shaped member 38 may further be arranged with distally directed arms 42. In the embodiment shown the ring-shaped member 38 comprises two distally directed arms 42. As shown in FIG. 3, the distal parts of the arms 42 may extend into longitudinal cut-outs or grooves 44 of the interlock member 46. The actuation member 48 may be provided through the interlock member 46. The actuation member 48 may comprise a generally tubular distal part arranged with protrusions 52 on its outer surface, wherein said protrusions 52 fit into the grooves 44 of the interlock member 46 as well into transversally extending grooves 47 on the interlock member 46, forming an interlock connection. The tubular part of the actuation member 48 may extend in the distal direction forming a push button 54, which protrudes through the interlock member towards the distal direction. Through holes 39 are arranged on the tubular part of the actuation member 48, the function of which will be explained below. The connection between the interlock member 46 and the housing is such that the interlock member is prevented to be detached from the housing but allowed to be rotated in relation to the housing. The connection between the interlock member and the actuation member 48 is such that the actuation member is allowed to be moved, more particularly axially slidable, in relation to the interlock member. The interlock member is also allowed to be rotated in relation to the actuation member.

The actuation member 48 comprises at least one latching projection 58 pointing in a generally distal direction but with a certain inclination in relation to the longitudinal axis L of the device. The at least one latching projection 58 is in the embodiment shown, FIG. 6, integrated in proximally directed arms 60 of the actuation member 48. Each latching projection 58 comprises at least one flexible section 62 and an end surface 63, the latter facing in the distal direction of the device.

Figure 4:
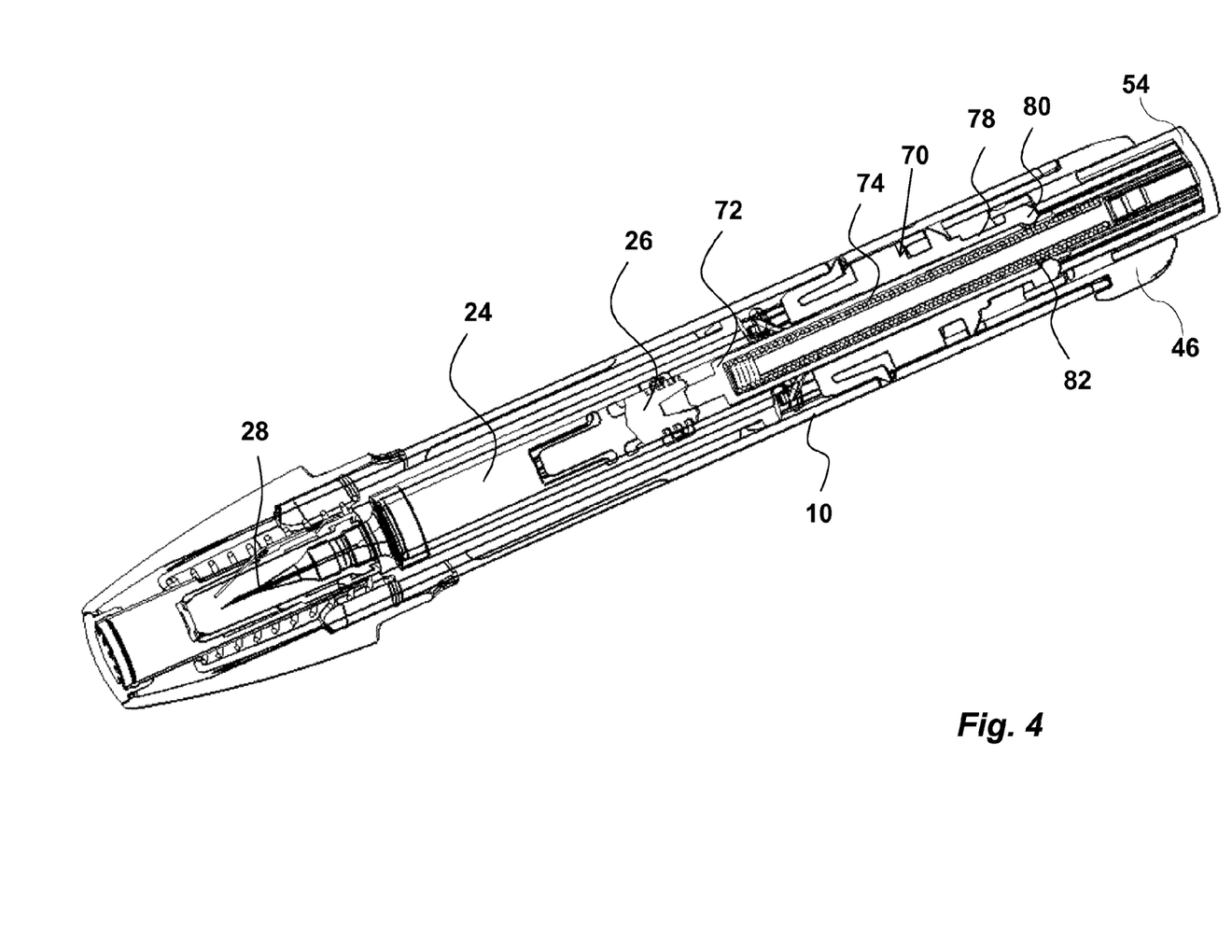
FIG. 4 is a cross-sectional view of the device of FIG. 1, and FIGS. 5-7 are detailed views showing different functional states of the device of FIG. 1.
Figure 5:
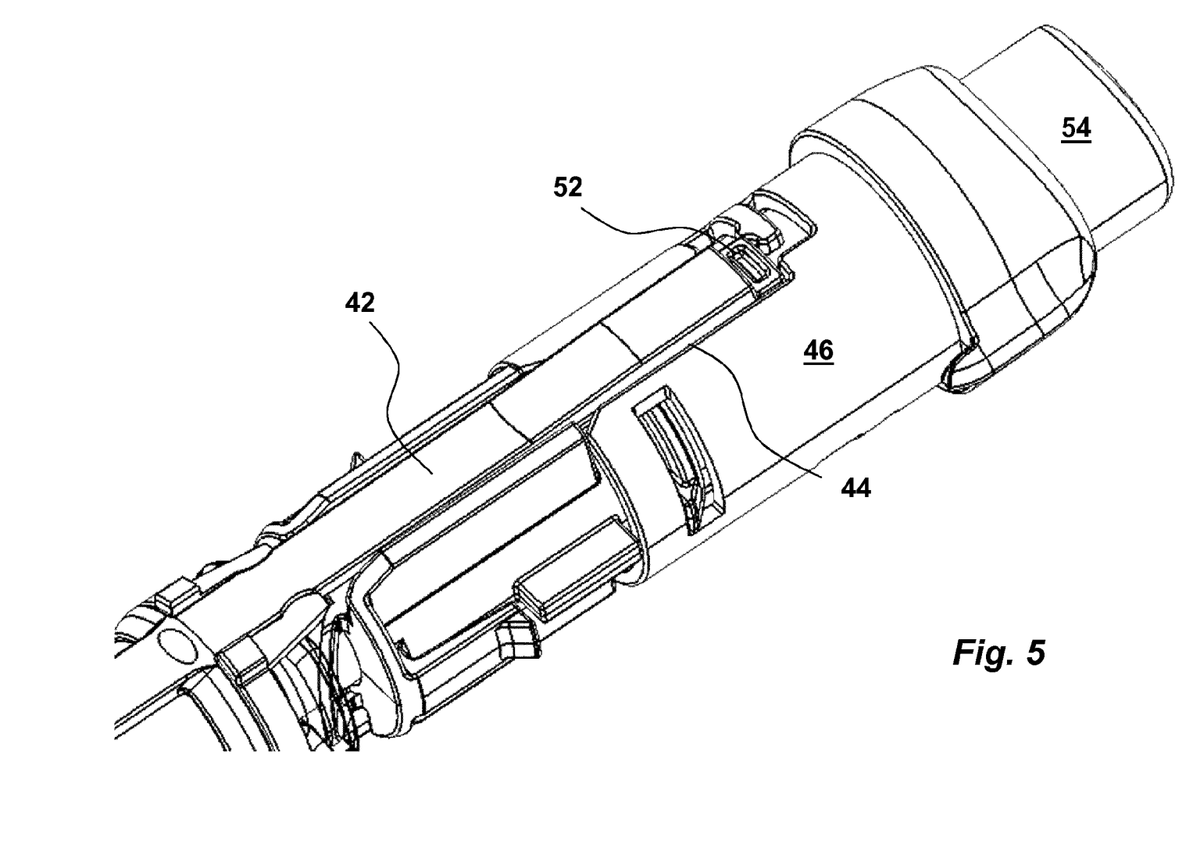

The device may be further provided with a drive mechanism 90 comprising a holding member 70, a plunger member or an elongated plunger rod 72, a drive spring 74, and a signal generating member 76, FIGS. 2 and 4. The plunger rod 72 may be provided with a hollow space into which the drive spring 74 is arranged to spring-load the plunger rod 72. The proximal end of the elongated plunger rod 72 may be in contact with the stopper 26 of the medicament container 24. A distal end of the drive spring 74 may be in contact with a transversal part of the signal generating member 76 which has a general U-shape. The signal generating member 76 may have proximally directed legs and each leg may comprise a radial outwardly extending ledge. The signal generating member 76 may be configured to partially surround the spring-loaded plunger rod. The holding member 70 comprises at least one, and more particularly two, distally directed arms 78 which may be flexible in the radial direction. The distal ends of the arms 78 may be arranged with inwardly directed hooks 80 and outwardly directed protrusions 79. The hooks 80 may be designed to fit into cut-outs or through holes 82 of the plunger rod 72 to hold it in position, FIG. 4, as will be explained. The protrusions 79 may be designed to interact with the inner surface of the tubular part of the actuation member 48 and with the through holes 39, arranged on the tubular part of the actuation member 48. The signal generating member 76 may be axially arranged through the holding member 70. The proximally directed arms 60 of the actuation member 48 may axially and slidably extend along grooves 66 on the outer surface of the holding member.

Moreover, the actuation member 48 is configured to be movable from a first position, in which it allows the drive mechanism to be retained, to a second position, in which it allows the drive mechanism 90 to be released, such that the medicament is allowed to be expelled through the delivery member 28. The actuation member is in the first position when said actuation member is arranged surrounding said distally directed arms 78 such that the hooks 80 are engaged into the cut-outs or through holes 82 of the plunger rod, and the protrusions 52 are aligned with the transversal grooves 47. The actuation member is in the second position when said push button 54 is completely positioned within the interlock member such that the protrusions 79 are allowed to come into the through holes 39 of the actuation member i.e. the through holes 39 are aligned with the protrusions 39 whereby the arms 78 are allowed to be moved radially outwards for allowing the hooks 80 to come out of engagement with the plunger rod.

Moreover, the interlock member 46 is configured to be movable between a locking position, at which it prevents movement of the actuation member 48 from its first position to its second position, and a releasing position, at which it allows movement of the actuation member 48 from its first position to its second position. The device has an indicator to show that it has been used, provided by the actuation member 48 being retained in its second position.

The interlock member 46 is in the locking position, when the protrusions 52 are positioned within the transversally extending grooves 47. The interlock member 46 is in the releasing position, when the protrusions 52 are positioned in line with the longitudinally extending grooves 44.

When the drive mechanism is assembled, the drive spring 74 may be compressed between a proximal inner end surface of the plunger rod 72 and the transversal part of the signal generating member 76. The radial outwardly extending ledges of the of the signal generating member 76 may be engaged to the proximal annular surface of the holding member 70 for preventing the signal generating member 76 from being moved in the distal direction by the drive spring 74. The plunger rod is thereby spring-biased in the proximal direction. As explained above, the actuation member 48 may be arranged surrounding said distally directed arms 78 such that the hooks 80 are engaged in a corresponding engagement with a cut-out 82 on said spring-loaded plunger rod. This means that the actuation member 48 is in the first position, in which it allows the drive mechanism to be retained. The protrusions 52 of the actuation member 48 are positioned into the grooves 44 of the interlock member 46 such that said interlock member 46 is in the locking position, at which it prevents movement of the actuation member 48 from its first position to its second position.

The arms 42 extend into longitudinal grooves 44 of the interlock member 46 over the proximally directed arms 60 of the actuation member 48, such that the distal end surfaces of the arms 42 are in line with the proximal edge of the transversal grooves 47 of the interlock member 46.

The distally directed surfaces 63 of the latching projections 58 are arranged to cooperate with latching surfaces 64 of the drive mechanism. More particularly, the latching surfaces 64 may be proximally directed surfaces of an annular ledge 68 on the outer surface of the holding member 70. The annular ledge 68 is arranged with cut-outs having side surfaces 65 through which cut-outs the proximally directed arms 60 of the actuation member 48 may extend. More particularly, said latching surfaces 64 are facing in the proximal direction of the device.

The device is intended to function as follows. When the device is to be used, the protective cap 20 is removed. In order to perform a dose delivery, the device has to be activated, which is done by turning the interlock member 46 in relation to the actuation member 48. This causes the transversal grooves 47 to slide in relation to the protrusions 52 until said protrusions 52 are in line with the longitudinal grooves 44 of the interlock member 46 such that the protrusions 52 abut the distal en surfaces of the of the arms 42. This means that the interlock member 46 has been moved from the locking position, at which it prevents movement of the actuation member 48 from its first position to its second position, to the releasing position, at which it allows movement of the actuation member 48 from its first position to its second position. However, the push button 54 is prevented to be depressed, since the proximally directed tongues 40 abut the ledge 34. To allow the push button to be depressed, the proximal end of the guard 14 needs to be pressed against the dose delivery site. This causes the guard 14 to axially slide towards the distal direction of the device in relation to the housing and the container holder whereby the distally directed tongues 16 will be moved in contact with the ledge 34. Since the ledge 34 is wedge-shaped, the tongues 16 will slide onto the ledge 34, exerting a radial force on the ledge 34 and thus on the distal end of the beam 32, deflecting the distal end of the beam, together with the ledge, radially inwards.

After the ledge 34 has been moved radially inwards, the proximally directed tongues 40 of the actuation locking member 36 no longer abut the ledge 34 allowing the actuation locking member 36 to be moved in the proximal direction. Thus, when the push button 54 is pressed in the proximal direction, the protrusions 52 are guided in the longitudinal grooves 44. Since the protrusions 52 are abutting the distal end surfaces of the arms 42, the ring-shaped member 38 is moved in the proximal direction, FIG. 4. Further, the displacement of the push button 54 towards the proximal end of the device, such that said push button is completely positioned within the interlock member 46, allows the protrusions 79 to come into the through-holes 39 such that the arms 78 are moved radially outwards allowing the hooks 80 to come out of engagement with the plunger rod 72. This means that the actuation member is in the second position. Having the push button completely positioned within the interlock member 46 means that no part of the push button protrudes distally of the interlock member, i.e. the transversal distal outer surface of the push button is flush with the distal annular edge of the interlock member 46. The plunger rod 72 may, after disengagement of the hooks 80, be forced in the proximal direction by the drive spring 74 and may act on the stopper 26 inside the medicament container 24 for delivering a dose of medicament through the medicament delivery member 28 at the dose delivery site. This means that the actuation member 48 has been moved from the first position, in which it allows the drive mechanism 90 to be retained, to a second position, in which it allows the drive mechanism 90 to be released, such that the medicament is expelled through the delivery member 28. The proximal movement of the ring-shaped member 38 causes the proximally directed tongues 40 to move in the proximal direction, whereby it may be moved radially outside the ledge 34, such that said ledge is held, pressed inwards in the radial direction.

According to the invention, when the push button 54 is moved in the proximal direction, so are the arms 60 with the latching projections 58. The latching projections will slide along, and be biased by, the side surfaces 65, FIGS. 6 and 7, of the cut-outs in the annular ledge 68 on the outer surface of the holding member 70. When the push button 54 has been pressed a certain distance in the proximal direction, the distal end surfaces 63 of the latching projections 58 have passed the cut-outs, the flexible sections 62 will urge the latching projections 58 back to its initial position. Now, as seen in FIG. 7, the distally directed end surfaces 63 of the latching projections 58 are abutting the proximally directed surfaces 64 of the annular ledge 68. This means that the latching projections 58 of the actuation member and the corresponding latching surfaces 64 of the drive mechanism latches when the actuation member 48 is in its second position.

In this position, the dose of medicament has been delivered, which is indicated by the actuation member 48 and thus the push button 54 being retained in the pressed, second position. It is thus obvious that the device has been used and has to be discarded. In this respect, the side surface of the push button 54 may be arranged with colouring indicating an unused, or ready-to-use, device, while, in the used position, the colouring is no longer visible since the push button 54 is inside the housing 10. This means that the device, or more particularly the actuation member, has an indicator to show that the device has been used.

When the dose has been delivered, the device may be withdrawn from the dose delivery site. This in turn causes the guard 14 to be moved in the proximal direction, relative to the housing and the container holder, by the guard spring 18. The proximal movement of the guard 14 will cause the proximal end of the beam 32 to be released, whereby the latter will flex outwards in the radial direction due to the tension built up in the beam 32 by the proximally directed tongues 40 when moved over the ledges 34. The beam 32, may thus reach a final position in which the proximal end of the beam 32 restricts the movement of guard 14 in the distal direction. The proximal end of the longitudinal beam 32 may be positioned between the distally directed tongues 16 of the guard 14, locking the guard 14 against movement in the distal direction and allowing the device to be discarded safely.

Figure 6:
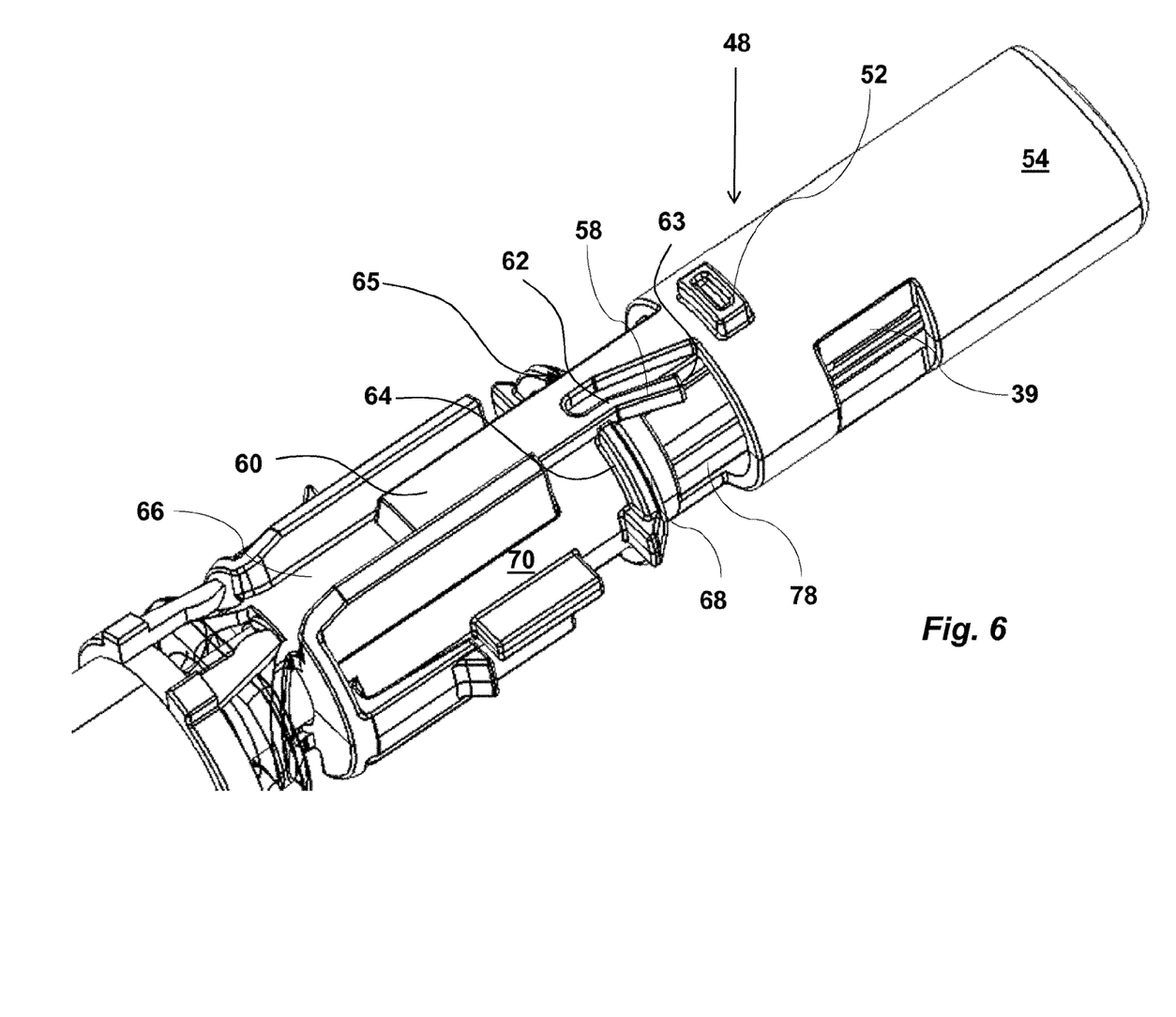
Figure 7:
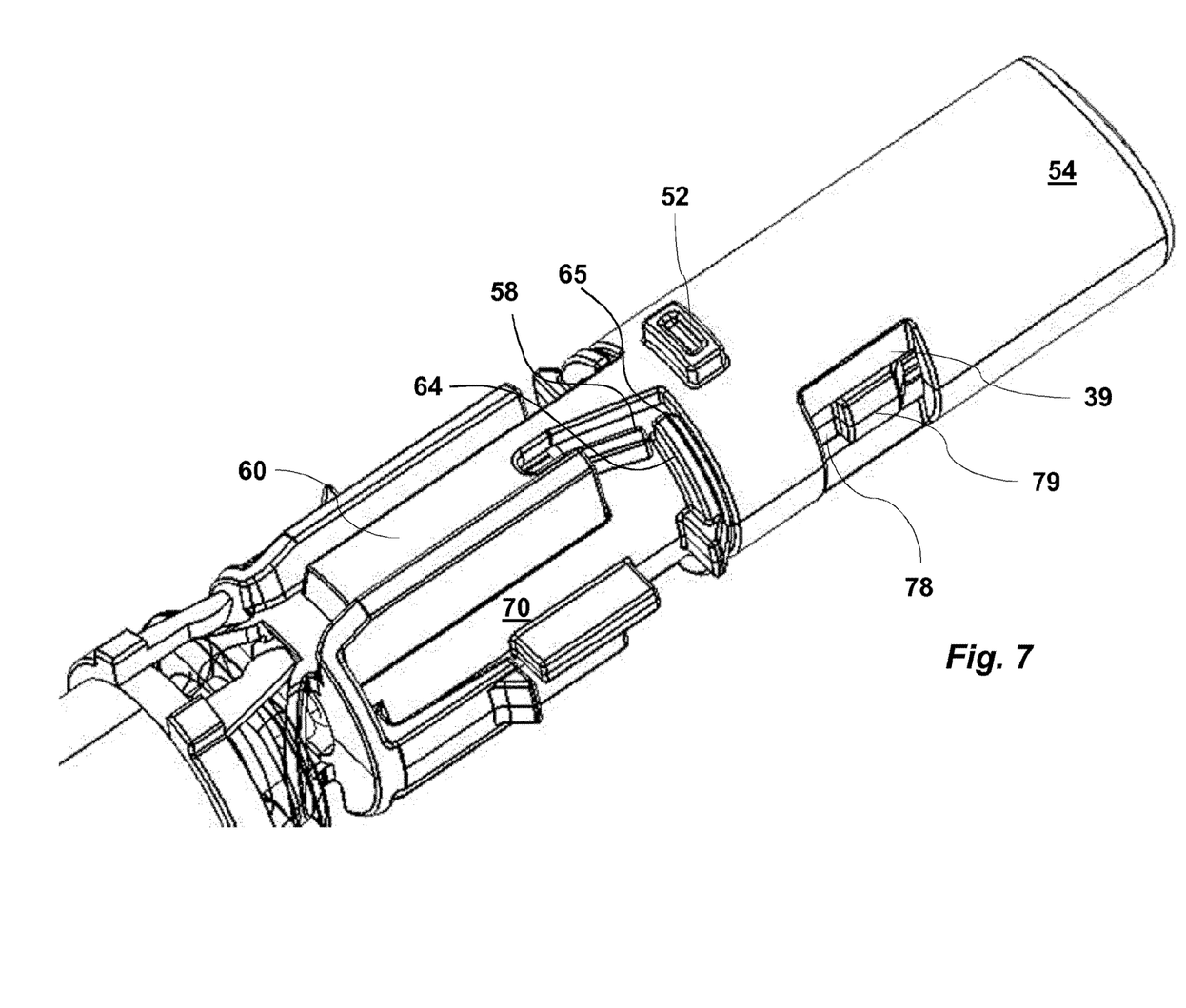
Figure 8:
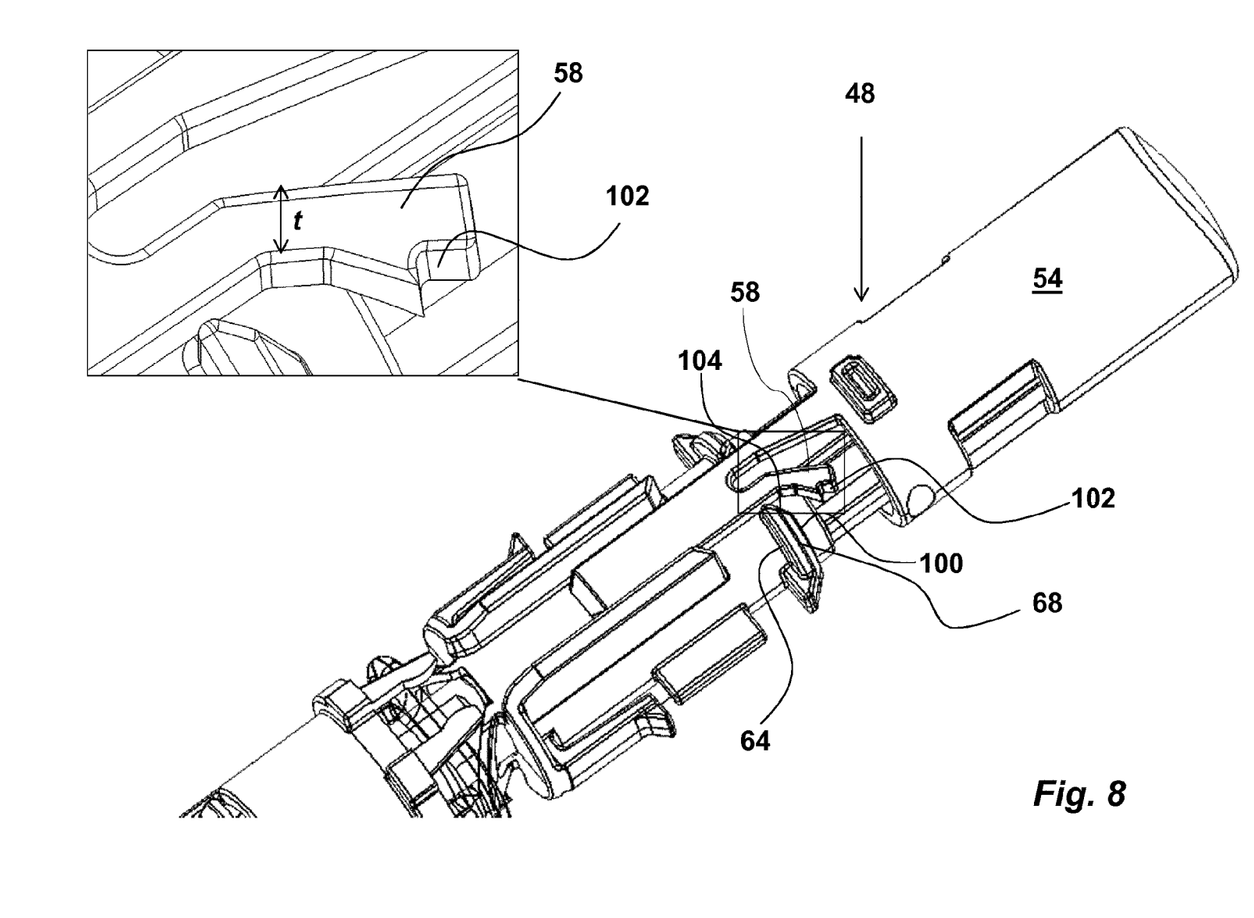
FIGS. 8-9 are detailed views showing different functional states of a variant of the embodiment of FIG. 1.
Figure 9:
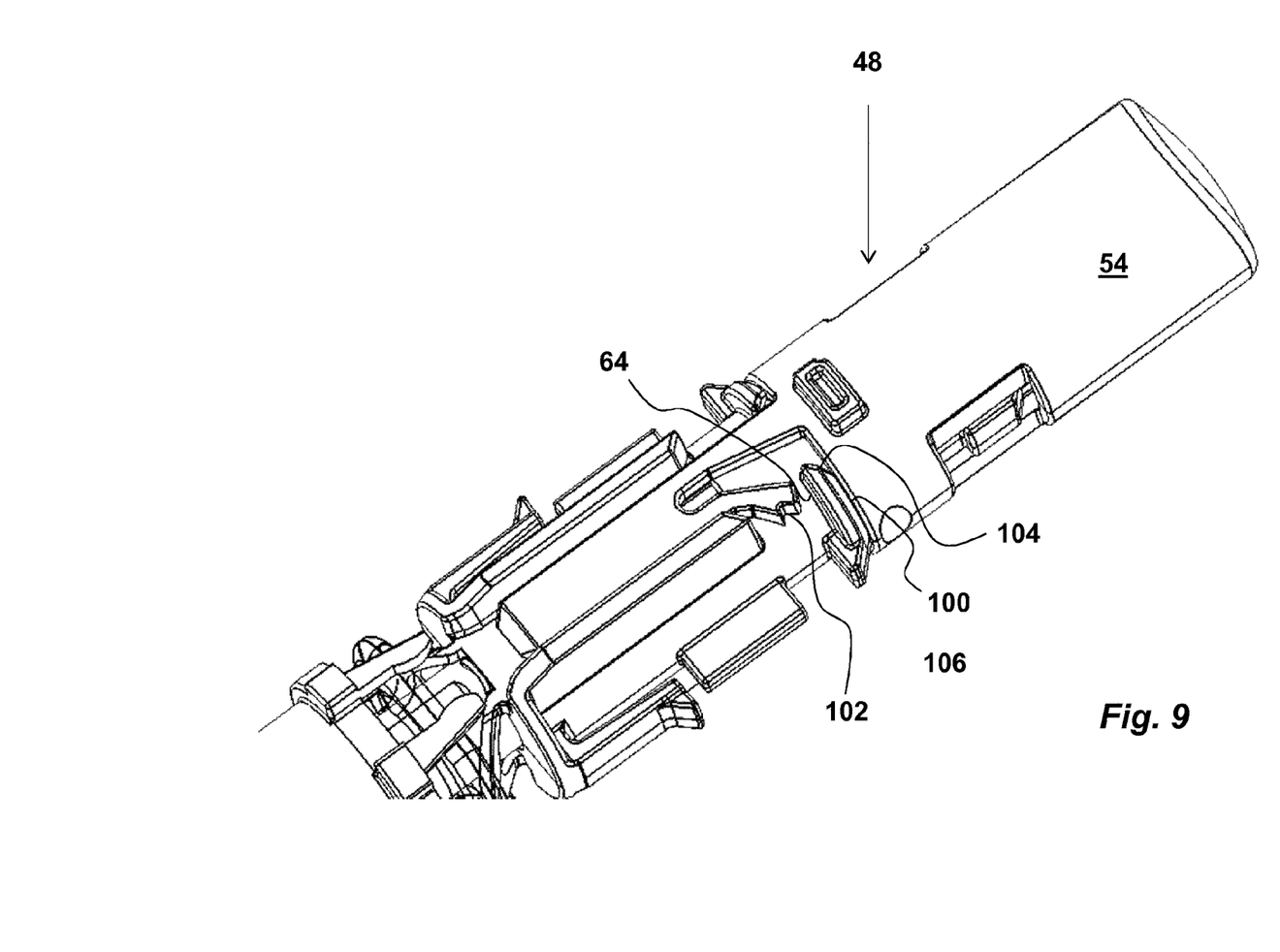

FIGS. 8-9 show a variant of the latching surface 64 and latching projection 64 to the present invention wherein the distal contact surface 100 of the annular ledge 68 according to FIG. 6 is arranged with a slanted or inclined section 104. Further, the latching projection 58 is arranged with a cut-out or notch 102. Thus, during actuation of the push button 54, the notch 102 in said latching projection 58 is caused to engage the slanted section 104 of said annular ledge 68 such that the contact between the notch 102 and the end surface of the slanted section 104 will resiliently push aside the latching projection 58 and then cause it to snap back against the slanted section 104 to provide both audible and tactile information to the user of the progress of the dose delivery sequence. Also, as with the previous variant, the device actuation member 48 is prevented from moving from its second position. Furthermore, in the variant shown in FIGS. 8 and 9, the latching projection 58 has an increased thickness t to further secure the device actuation member 48 in its second position.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
a housing configured to receive a medicament container;
a drive mechanism that interacts with the medicament container, wherein the drive mechanism comprises at least one latching surface, a holding member, and a plunger member;
an actuation member that is movable from a first position, in which the actuation member enables the drive mechanism to be retained, to a second position, in which the actuation member enables the drive mechanism to be released, such that medicament in the medicament container is enabled to be expelled through a delivery member;
an interlock member that is movable between a lock position, in which the interlock member prevents movement of the actuation member from the first position to the second position, and a release position, in which the interlock member enables movement of the actuation member from the first position to the second position; and
wherein the actuation member retained in the second position indicates that the medicament delivery device has been used; the actuation member comprises at least one latching projection that latches against the at least one latching surface when the actuation member is in the second position; and the holding member comprises a first engagement member configured to engage the plunger member when the actuation member is in the first position and to disengage the plunger member and engage the actuation member when the actuation member is in the second position; and
the at least one latching projection comprises at least one flexible section and an end surface that faces in a distal direction of the medicament delivery device; the at least one latching projection is integrated in proximally directed arms of the actuation member; the at least one latching surface faces in a proximal direction of the medicament delivery device such that the at least one latching surface and the end surface are brought in latching engagement when the actuation member is in the second position; and the at least one latching surface includes at least one proximally directed surface of an annular ledge on an outer surface of the holding member.

2. The medicament delivery device of claim 1, wherein the drive mechanism comprises a drive spring, and a signal generating member.

3. The medicament delivery device of claim 1, wherein the annular ledge includes cut-outs having side surfaces and through which the proximally directed arms of the actuation member are extendable.

4. The medicament delivery device of claim 3, wherein the at least one latching projection is configured to be biased by the side surfaces when the actuation member is moved a certain distance from the first position to the second position and such that when the end surface of the at least one latching projection has passed the cut-outs, the at least one flexible section biases back the at least one latching projection, whereby the end surface of the at least one latching projection latches with the at least one proximally directed surface of the annular ledge.

5. The medicament delivery device of claim 4, wherein the at least one latching projection includes a notch configured to provide tactile and audible response when passing the side surfaces.

6. The medicament delivery device of claim 5, wherein one of the side surfaces includes a slanted section.

7. The medicament delivery device of claim 1, wherein the medicament delivery device is an injection device.

8. The medicament delivery device of claim 7, wherein the injection device is a pen injector or an auto-injector.

9. A medicament delivery device, comprising:
- a housing configured to receive a medicament container;
- a drive mechanism that interacts with the medicament container, wherein the drive mechanism comprises at least one latching surface, a holding member, and a plunger member;
- an actuation member that is movable from a first position, in which the actuation member enables the drive mechanism to be retained, to a second position, in which the actuation member enables the drive mechanism to be released, such that medicament in the medicament container is enabled to be expelled through a delivery member; and
- an interlock member that is movable between a lock position, in which the interlock member prevents movement of the actuation member from the first position to the second position, and a release position, in which the interlock member enables movement of the actuation member from the first position to the second position;
- wherein the actuation member retained in the second position indicates that the medicament delivery device has been used; the actuation member comprises at least one latching projection that latches against the at least one latching surface when the actuation member is in the second position; the holding member comprises a first engagement member configured to engage the plunger member when the actuation member is in the first position and to disengage the plunger member and engage the actuation member when the actuation member is in the second position; the actuation member comprises a generally tubular distal part forming a push button provided through the interlock member; and the generally tubular distal part has an outer surface that includes protrusions configured to fit into transversal and longitudinal grooves of the interlock member.

10. The medicament delivery device of claim 9, wherein when the interlock member is in the lock position, the protrusions are positioned in the transversal grooves, and when the interlock member is in the release position, the protrusions are positioned in line with the longitudinal grooves.

11. A medicament delivery device, comprising:
- a housing configured to receive a medicament container;
- a drive mechanism that interacts with the medicament container;
- an actuation member that is movable from a first position, in which the actuation member enables the drive mechanism to be retained, to a second position, in which the actuation member enables the drive mechanism to be released, such that medicament in the medicament container is enabled to be expelled through a delivery member;
- an interlock member that is movable between a lock position, in which the interlock member prevents movement of the actuation member from the first position to the second position, and a release position, in which the interlock member enables movement of the actuation member from the first position to the second position; and
- wherein the actuation member retained in the second position indicates that the medicament delivery device has been used; the actuation member comprises at least one latching projection; the drive mechanism comprises at least one latching surface against which the at least one latching projection latches when the actuation member is in the second position; the at least one latching projection comprises at least one flexible section and an end surface that faces in a distal direction of the medicament delivery device; the at least one latching projection is integrated in proximally directed arms of the actuation member; the at least one latching surface faces in a proximal direction of the medicament delivery device such that the at least one latching surface and the end surface are brought in latching engagement when the actuation member is in the second position; the drive mechanism comprises a holding member, a plunger member, a drive spring, and a signal generating member; and the holding member comprises at least one distally directed arm that includes inwardly directed hooks configured to fit into cut-outs or through-holes of the plunger rod and outwardly directed protrusions that interact with an inner surface of the actuation member and with through-holes of the actuation member.

12. The medicament delivery device of claim 11, wherein when the actuation member is in the first position, the actuation member is configured to surround the at least one distally directed arm such that the hooks are engaged into the cut-outs or through-holes of the plunger rod.

13. The medicament delivery device of claim 11, wherein when the actuation member is in the second position, a push button is configured to be completely positioned within the interlock member such that the protrusions enter the through-holes of the actuation member, whereby the at least one distally directed arm is enabled to move radially outward for disengaging the hooks from the plunger rod.

* * * * *